(12) United States Patent
Boekelheide et al.

(10) Patent No.: US 12,241,049 B2
(45) Date of Patent: Mar. 4, 2025

(54) MULTI-COMPARTMENT DEVICE CONTAINING HUMAN THREE-DIMENSIONAL (3D) MICROTISSUES FOR TOXICITY TESTING

(71) Applicant: BROWN UNIVERSITY, Providence, RI (US)

(72) Inventors: Kim Boekelheide, East Greenwich, RI (US); Jeffrey Morgan, Sharon, MA (US); Susan Hall, Saunderstown, RI (US); Hui Li, Cranston, RI (US); Blanche Ip, Providence, RI (US)

(73) Assignee: BROWN UNIVERSITY, Providence, RI (US)

( * ) Notice: Subject to any disclaimer, the term of this patent is extended or adjusted under 35 U.S.C. 154(b) by 781 days.

(21) Appl. No.: 17/420,107

(22) PCT Filed: Jan. 9, 2020

(86) PCT No.: PCT/US2020/012986
§ 371 (c)(1),
(2) Date: Jun. 30, 2021

(87) PCT Pub. No.: WO2020/146676
PCT Pub. Date: Jul. 16, 2020

(65) Prior Publication Data
US 2022/0081659 A1    Mar. 17, 2022

Related U.S. Application Data

(60) Provisional application No. 62/790,901, filed on Jan. 10, 2019.

(51) Int. Cl.
*C12M 3/00*    (2006.01)
*C12M 1/00*    (2006.01)
(Continued)

(52) U.S. Cl.
CPC ............ *C12M 21/08* (2013.01); *C12M 23/12* (2013.01); *C12M 23/34* (2013.01); *C12M 35/08* (2013.01);
(Continued)

(58) Field of Classification Search
None
See application file for complete search history.

(56) References Cited

U.S. PATENT DOCUMENTS 8,361,781 B2    1/2013    Morgan et al.
8,501,476 B2    8/2013    Morgan et al.
(Continued)

FOREIGN PATENT DOCUMENTS

JP    2007215472 A  *  8/2007    ............ C12M 23/10
WO    2005034624 A2    4/2005
(Continued)

OTHER PUBLICATIONS

Desroches et al., "Functional Scaffold-Free 3-D Cardiac Microtissues: A Novel Model for the Investigation of Heart Cells", American Journal of Physiology, vol. 302, Issue 10, pp. H2031-H2042, Mar. 16, 2012.
(Continued)

*Primary Examiner* — William H. Beisner
(74) *Attorney, Agent, or Firm* — Adler Pollock & Sheehan P.C.

(57) ABSTRACT

This dual-compartment liver co-culture system exposes target microtissue to metabolites, allowing for evaluating toxicity using a standard multi-well plate for high throughput analysis. Discovery scientists can rapidly select lead compounds with desirable metabolic profiles, while safety scientists can determine the safety of drugs, pesticides, and environmental chemicals. This platform is allometrically scalable, so it can mimic the natural size differences between
(Continued)

healthy organs and, with the liver, produce sufficient quantities of metabolites. The device is simple to use and designed for immediate in vitro pathology assessment using confocal microscopy, transcriptomics, and proteomics.

7 Claims, 4 Drawing Sheets

(51) Int. Cl.
  *C12M 1/32* (2006.01)
  *C12M 1/42* (2006.01)
  *G01N 33/50* (2006.01)
(52) U.S. Cl.
  CPC ..... *G01N 33/5014* (2013.01); *G01N 33/5088* (2013.01)

(56) References Cited

U.S. PATENT DOCUMENTS

| | | |
|---|---|---|
| 9,468,680 B2 | 10/2016 | Morgan et al. |
| 9,587,213 B2 | 3/2017 | Morgan et al. |
| 9,771,554 B2 | 9/2017 | Morgan et al. |
| 10,073,346 B2 | 9/2018 | Hribar et al. |
| 11,286,451 B2 | 3/2022 | Morgan et al. |
| 2007/0141555 A1* | 6/2007 | Deutsch ............... B01L 3/5085 435/287.1 |
| 2013/0029412 A1* | 1/2013 | Reis .................... C12M 25/04 422/561 |
| 2016/0282338 A1 | 9/2016 | Miklas et al. |
| 2017/0152474 A1 | 6/2017 | Forgacs et al. |

FOREIGN PATENT DOCUMENTS

| | | |
|---|---|---|
| WO | 2007087402 A2 | 8/2007 |
| WO | 2013086329 A1 | 6/2013 |

OTHER PUBLICATIONS

Mondrinos et al., "Native Extracellular Matrix-Derived Semipermeable, Optically Transparent, and Inexpensive Membrane Inserts for Microfluidic Cell Culture", Lab Chip, vol. 17, Issue 18, pp. 3146-3158, Sep. 12, 2017.

International Search Report and Written Opinion received in International Application No. PCT/US2020/012986 mailed on May 20, 2020, 9 Pages.

Curran, et al. "A 3D Spheroid System to Evaluate Inhibitors of the ABCG2 Transporter in Drug Uptake and Penetration", Technology, vol. 3, No. 1, pp. 54-63, Mar. 2015.

Robins, et al. "Bioengineering Anembryonic Human Trophoblast Vesicles", Reproductive Sciences, vol. 18, Issue 2, pp. 128-135, Oct. 26, 2010.

Bao, et al. "Connexon-mediated Cell Adhesion Drives Microtissue Self-assembly", The FASEB Journal, vol. 25 pp. 1-10, Sep. 27, 2010.

Dean, et al. "Rods, Tori, and Honeycombs: the Directed Self-assembly Of Microtissues With Prescribed Microscale Geometries", The FASEB Journal, vol. 21, pp. 4005-4012, Dec. 2007.

Birenboim, et al. "Simple Generation of Neurons From Human Embryonic Stem Cells Using Agarose Multiwell Dishes", Journal of Neuroscience Methods, vol. 214, pp. 9-14, 2013.

Dingle, et al. "Three-dimensional Neural Spheroid Culture: an in Vitro Model for Cortical Studies", Tissue Engineering: Part C, vol. 21, No. 12, pp. 1-10, Oct. 6, 2015.

Masuda, et al. "Toroidal Cellular Aggregates for Directed Assembly of Multicellular Structure", 15th International Conference on Miniaturized Systems for Chemistry and Life Sciences, pp. 163-166, Oct. 2-6, 2011.

Ramaiahgari, et al., "Three-Dimensional (3D) HepaRG Spheroid Model with Physiologically Relevant Xenobiotic Metabolism Competence and Hepatocyte Functionality for Liver Toxicity Screening", Toxicological Sciences, vol. 159, No. 1, 2017, pp. 124-136.

\* cited by examiner

MULTI-COMPARTMENT DEVICE CONTAINING HUMAN THREE-DIMENSIONAL (3D) MICROTISSUES FOR TOXICITY TESTING

CROSS REFERENCE TO RELATED APPLICATIONS

This application is a national phase filing under 35 U.S.C. § 371 of International Application No. PCT/US2020/012986 filed Jan. 9, 2020, which claims priority from U.S. Provisional Patent Application No. 62/790,901 filed Jan. 10, 2019, the entire contents of which are hereby incorporated by reference herein.

STATEMENT REGARDING FEDERALLY SPONSORED RESEARCH OR DEVELOPMENT

This invention was made with government support under grant no. 1 U01 ES028184-01 awarded by the National Institutes of Health. The government has certain rights in the invention.

TECHNICAL FIELD OF THE INVENTION

This invention generally relates to the cell culture or maintenance thereof of human or animal cells or tissues, and the cultivation or culture media therefor. This invention also relates generally to well or multi-well plates.

BACKGROUND OF THE INVENTION

Liver toxicity is a significant reason many new drugs fail in clinical trials. Often, new drugs or new chemicals are not toxic until the liver metabolizes them and converts them into toxic metabolites.

Primary human hepatocytes (PHHs) are currently a "gold standard" for in vitro liver models. Still, PHH use for chemical safety evaluation is limited by donor-specific variability, a finite supply from individual donors, and rapidly losing hepatocyte functionality in vitro. Immortalized cells are alternatives to PHHs in screening assays. However, immortalized cells sometimes have low or undetectable levels of drug or xenobiotic metabolism enzymes and a high degree of karyotype abnormalities. Recent advances with "next-generation" in vitro models using micro-patterning, extracellular gel matrices, bio-printing, and other approaches have improved longevity and differentiation states with PHHs and immortalized cell lines. Most of these approaches currently lack the throughput necessary to assess concentration-response and time or simplicity in design for predictive toxicology/pharmacology screening.

Thus, there remains a need in the toxicity testing art for simple 3D human microtissues (prostate, ovary, lung, brain, and heart) that can be interrogated for in vitro pathology, using molecular and functional endpoints to identify adverse effects.

SUMMARY OF THE INVENTION

The invention provides, in a first embodiment, a multi-compartment device (e.g., a two-compartment device) containing three-dimensional (3D) metabolizing and hormone-producing microtissues in a first compartment and a selected target cell in a second compartment, with a permeable wall between the first compartment and the second compartment. The first compartment can be seeded with cells from a metabolizing and hormone-producing cell population. The second compartment can be seeded with cells from a selected target cell population. When a test compound is added to the first compartment, the metabolizing and hormone-producing microtissue metabolizes the test compound. Then, the metabolites freely and passively diffuse between the two compartments, through the permeable wall to the second compartment and from the second compartment into the first compartment, to mediate an effect on the target microtissue. Thus, this invention can be a sensitive bioassay to screen rapidly for toxic metabolites. The invention advantageously enhances the usefulness of microtissues for more widespread biological applications in vitro.

In a second embodiment, the invention provides a device, being a platform that incorporates human liver metabolism for perturbing a target microtissue.

In a third embodiment, the 3D microtissue in the first component is allometrically scaled to deliver metabolites and to the target cell in the second compartment. In vitro models must be appropriately scaled to recreate interactions (metabolically and physiologically) between tissue types, to recapitulate and be extrapolated to the in vivo reality. The liver is the major organ that contributes to the metabolism of biomolecules, including drugs and chemicals. The impact of liver-generated drug metabolites on other tissues depends significantly on the concentration of the synthesized metabolites. Based on prior studies by Ramaiahgari et al., Toxicol. Sci., 159, 124-136 (2017), and suggested by Bale et al., Tissue Engineering Part B: Reviews, 22(5), 383-394 (2016), the minimum cell-to-media ratio to achieve appropriate allometric scaling of the human liver is ~one hepatocyte/nL. This multi-compartment system in the 96-well plate format is flexible and sufficient to incorporate at least 200,000 hepatocytes in one compartment submerged in 200 µL of media. All 200,000 hepatocytes can be housed in one toroid-shaped compartment, or multiple compartments, depending on the assay needs. One having ordinary skill in the cell biological art can design geometries for the 384-well system while maintaining the same allometric scaling. The hepatocyte of choice includes, but is not limited to, primary human hepatocytes (PHH), iPS-derived hepatocytes, and HepaRG cells, which exhibit liver metabolism comparable to PHH. Also, hepatocytes can be combined with hepatic stromal cells, such as stellate cells and endothelial cells, depending on the needs of the in vitro system. Advantageously, the invention provides an in vitro 3D high-throughput predictive biology device for safety assessments, that provides a liver metabolizing capability in the microtissue plates.

In a fourth embodiment, the first compartment contains enough liver cells to ensure that metabolites are of high enough concentration to mediate effects, and the device has two distinct compartments that can be separately and sequentially seeded with different cell types.

In a fifth embodiment, the walls of the device between the first compartment and the second compartment comprise a non-adhesive hydrogel having sufficient porosity to permit metabolites and hormones from the 3D microtissues to diffuse from the first compartment to the second compartment and from the second compartment to the first compartment.

In a sixth embodiment, the device comprises a first compartment containing 3D metabolizing and hormone-producing microtissues in a culture medium; and the second compartment includes a selected target cell population in a culture medium.

In a seventh embodiment, the invention comprises a liver microtissue in a first compartment and a selected target microtissue in a second compartment with a permeable wall between the first compartment and the second compartment, which allows for a diffusion-driven exchange of metabolites between the two types of microtissues.

In an eighth embodiment, the invention provides an approximately proper allometric scaling of the liver microtissue, the volume of media, and the target tissue. This allometric scaling ensures that metabolites produced by the liver microtissue are of sufficient concentration to mediate an effect on the target tissue.

In a ninth embodiment, the invention is an integrated human liver plus target cell co-culture device designed to fit within a standard 96-well plate. The invention works in standard 96-well plates. The device is amenable to a high-throughput workflow and screening of test compounds by analytical techniques well known to the pharmaceutical industry, including liquid handling robots, confocal microscopy, automated microscopy, integrated imaging, molecular, and functional analyses. The device can also be configured to fit in a standard 384-well plate. Kabadi et al., BioTechniques, 59(5), 279-86 (2015), describes several materials, method, and techniques for in vitro three-dimensional microtissue visualization. The multi-compartment device in either the 96-well or the 384-well plate will house different tissues that can be generated either simultaneously or sequentially depending on assay needs. This device feature are be achieved by having different heights of the hydrogel walls for each compartment within one device. All the tissues within one device will be generated on the same z-plane. This design allows tissues to be imaged simultaneously on a confocal or non-confocal microscope while minimizing potential issues such as focusing during imaging, between tissues difference in losing fluorescence with depth, and differential nutrient diffusion.

In a tenth embodiment, the invention provides a method of making a device having at least a first compartment adapted for containing three-dimensional (3D microtissues and a second compartment adapted for holding three-dimensional (3D) microtissues of a selected target cell population, wherein metabolites and hormones from the 3D liver microtissues can passively diffuse from the first to the second compartment and from the second compartment to the first compartment. The steps of the method include (1) placing a mold that forms two compartments into a standard multi-well plate; (2) adding a liquid non-adhesive hydrogel to the mold in the well; and (3) allowing the non-adhesive hydrogel to harden, so the non-adhesive hydrogel has sufficient porosity to permit metabolites and hormones from the 3D microtissues to diffuse from the first compartment to the second compartment, and from the second compartment to the first compartment. One can use several different hydrogels in generating a device that is non-adhesive to cells, multi-compartmented to generate different tissues within one well. They would allow biomolecules to diffuse between the compartments through the hydrogel freely. These non-adhesive hydrogels include but are not limited to agarose, polyacrylamide, polyethylene glycol, alginate, and any combinations thereof.

In an eleventh embodiment, the invention provides a method for measuring the toxicity of a test compound. The steps include (a) obtaining the device of the invention; (b) adding the test compound to the first compartment, under conditions so the first compartment contains 3D microtissues in a culture medium; (c) permitting the metabolites from the 3D microtissues in the first compartment to diffuse to the second compartment, under conditions so the second compartment contains 3D microtissues of the selected target cell population in a culture medium; and (d) measuring the effect of the metabolites from the 3D microtissues in the first compartment on the 3D microtissues of the selected target cell population, using an assay that measures a morphological, molecular or functional endpoint, wherein the endpoint provides a safety assessment of the test compound.

In a twelfth embodiment, the assay is amenable to a high throughput workflow. Advantageously, the invention provides human 3D microtissues for toxicity testing by integrated imaging, molecular, and functional analyses.

In another aspect, the invention provides, besides three-dimensional×three-dimensional (3D-3D) embodiments, three-dimensional×two-dimensional (3D-3D) embodiments.

In a thirteenth embodiment, the invention provides a metal master mold for forming a two-compartment agarose device in a 96-well plate or a 384-well plate. The metal master mold is useful for forming a two-compartment device in each well of a 96-well plate or a 384-well plate.

In a fourteenth embodiment, the invention provides a two-compartment agarose device in a well of a 96-well plate or a 384-well plate. In a fifteenth embodiment, the invention provides a molded agarose gel comprising a first compartment capable of containing a three-dimensional (3D) ring of tissue and a second compartment capable of containing a three-dimensional (3D) spheroid of cells.

In a sixteenth embodiment, the invention provides a molded agarose gel comprising a first compartment containing a three-dimensional (3D) ring of tissue and a second compartment containing target cells that form a three-dimensional (3D) spheroid of cells.

In a seventeenth embodiment, the three-dimensional (3D) ring of tissue is a ring of liver tissue.

In an eighteenth embodiment, the invention provides a molded agarose gel comprising a first compartment containing a three-dimensional (3D) ring of tissue and a second compartment containing target cells where the target cells attach to the bottom of a 96-well plate or a 384-well plate.

In a nineteenth embodiment, a three-dimensional (3D) ring of tissue is a ring of liver tissue.

BRIEF DESCRIPTION OF THE DRAWINGS

FIG. 2 shows the results obtained during developing the invention.

Figure 3:
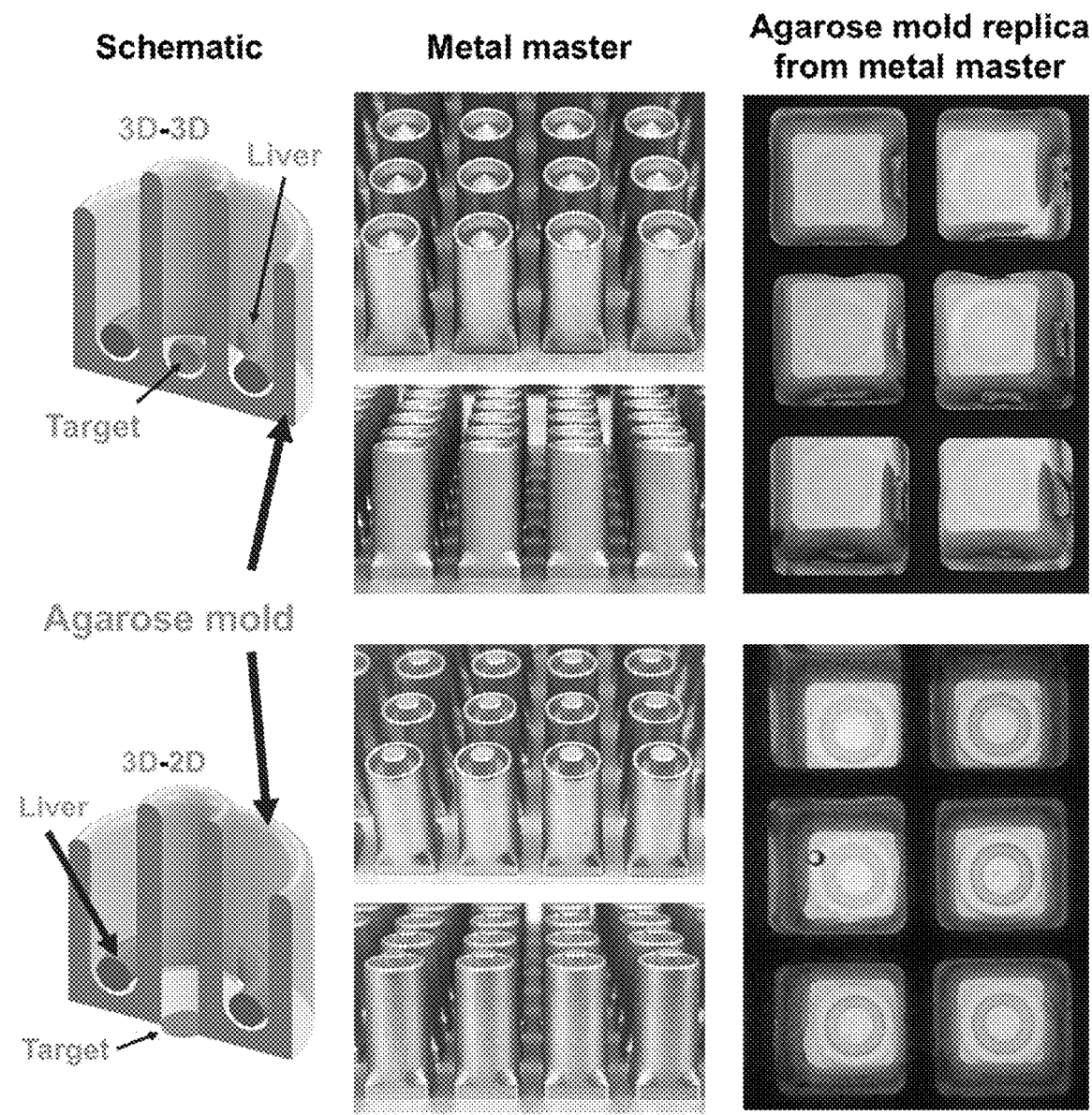
FIG. 3 shows data for two embodiments of the multi-compartment device and how to make them. The FIG. 3 top row, going left to right, shows a cross-sectional view of a schematic of an embodiment where the molded agarose gel has a 3D ring of liver tissue and a second compartment where the target cells form a 3D spheroid. Shown next to the right is a photograph of the metal master mold used to mold agarose in a 96-well plate to form the two-compartment device in each well of a 96-well plate. Next, to the right, is a photograph of six wells of a 96-well plate in each of which agarose has been molded to form this two-compartment device in each well.

The FIG. 3 bottom row, going left to right, shows a cross-sectional view of a schematic of an embodiment where the molded agarose gel has a 3D ring of liver tissue and a second compartment where the target cells attach to the bottom of a 96-well plate. Shown next to the right is a photograph of the metal master mold used to mold agarose in a 96-well plate to form this two-compartment device in each well of a 96-well plate. Next, to the right, is a photograph of six wells of a 96-well plate in each of which agarose has been molded to form this two-compartment device in each well.

Figure 4:
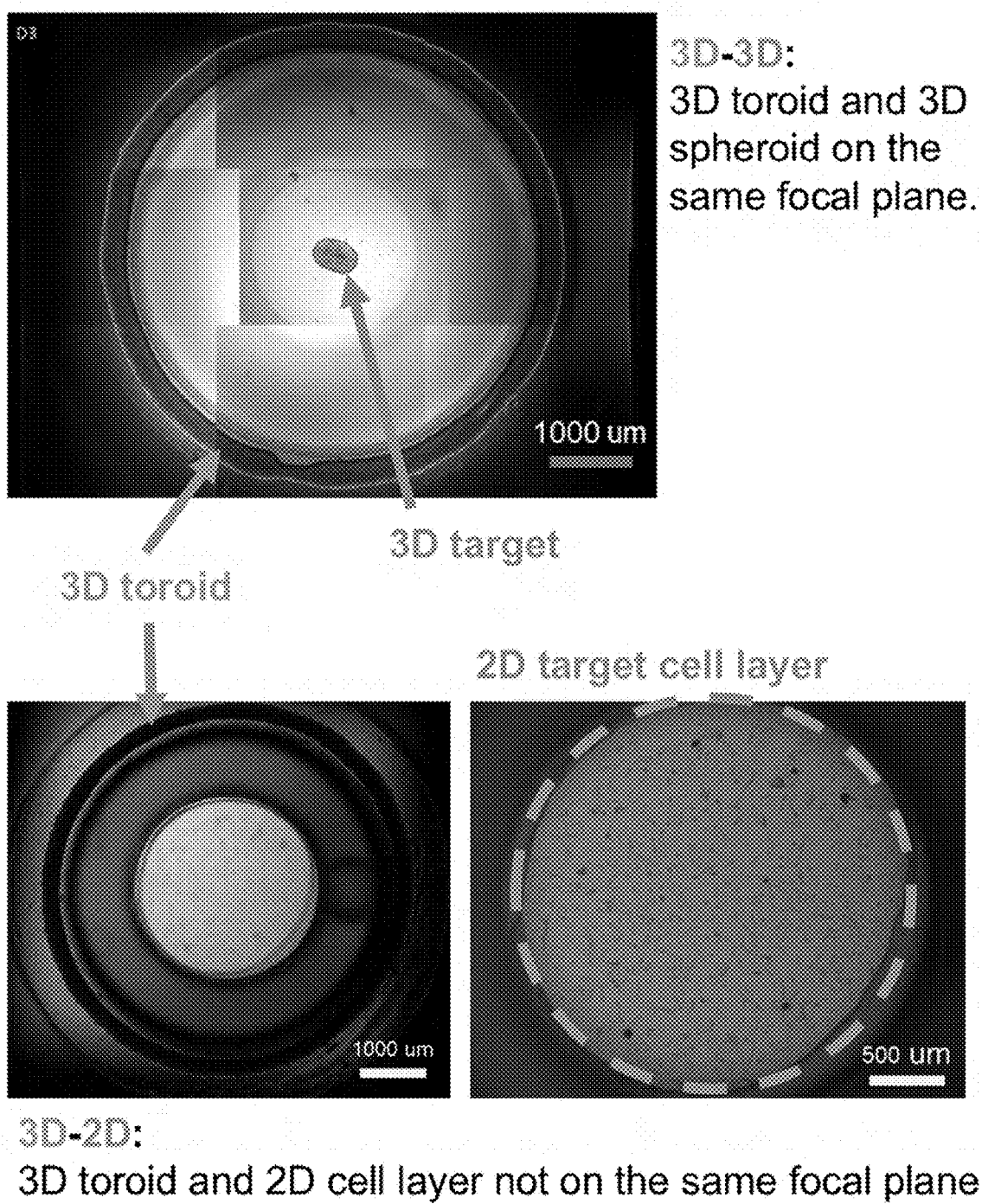

FIG. 4 shows data for two embodiments of the multi-compartment device and how to make them. FIG. 4, top row, is a phase-contrast image of a single well of a 96-well plate containing a two-compartment device molded from agarose and into which cells have been seeded separately into the two compartments. Cells seeded into the ring compartment of the device have formed a 3D ring-shaped tissue, whereas cells seeded into the center compartment have formed a 3D spheroid.

The FIG. 4 bottom row shows a pair of phase-contrast images of a single well of a 96-well plate containing a two-compartment device molded from agarose and into which cells have been seeded separately into the two compartments. Cells seeded into the ring compartment of the device have formed a 3D ring-shaped tissue, whereas cells seeded into the center compartment have attached and spread on the bottom of the 96-well plate.

DETAILED DESCRIPTION OF THE INVENTION

Industrial Applicability

This multi-compartment (e.g., dual compartment liver) co-culture system makes in vitro safety testing a reality, by measuring and integrating the biologic responses of miniaturized human tissues. The invention provides a cost-effective and predictive co-culture system that exposes the target cells to metabolites, allowing one of skill in the cell culture arts to evaluate toxicity using a standard multi-well plate for high throughput analysis. This platform is allometrically scalable, so it can mimic the natural size differences between healthy organs and, with the liver, produce sufficient quantities of metabolites. The device is simple to use for immediate in vitro pathology assessment using confocal microscopy, transcriptomics, and proteomics to identify pathologic responses to chemical and drug exposures.

There are many potential toxicants and drugs whose concentration-dependent effects are unknown. Discovery scientists can rapidly select lead compounds with desirable metabolic profiles, while safety scientists can determine the safety of drugs, pesticides, and environmental chemicals.

Through an interdisciplinary integration of biology and engineering, the inventors provide high-throughput cells as predictive biology platforms that reflect human physiology and disease, solving fundamental questions of adverse biological response. The invention advances state-of-the-art, humane approaches to understanding the essential characteristics of health and disease, including identifying alternatives to animal testing for screening of environmental toxicants and new drugs.

Definitions

"HepaRG" cells are bi-potent progenitor cells that can be expanded and differentiated into "differentiated" co-cultures of hepatocyte-like and cholangiocyte-like cells in 2D culture configurations. One can cryopreserve "fully" differentiated HepaRG cells, which can later be grown in differentiation medium to maintain drug metabolism activity and hepatocyte functionality. Cryopreserved differentiated HepaRG cells are commercially available from Triangle Research Labs, Durham NC, USA, which has been acquired by Lonza, Walkersville, MD, USA.

"Harden" has the plain meaning of making or becoming tougher and more clearly defined. One having ordinary skill in the cell biological art can harden agarose and alginate to form a device. One of ordinary skill in the cell biological art can polymerize polymeric precursors such as polyacrylamide precursor to cause them to harden and form a polymeric device.

"Hepatocyte" has the cell biological art-recognized definition of a cell of the main parenchymal tissue of the liver. Hepatocytes make up 55-65% of the liver's mass.

"Induced pluripotent stem cell" (also known as iPS cell or iPSC) has the art-recognized definition of a type of pluripotent stem cell that can be generated directly from adult cells.

"Liver tissue" is a population of cells derived from liver cells, the population having the functional properties of natural liver tissue. The liver's highly specialized tissue consisting of mostly hepatocytes regulates a wide variety of high-volume biochemical reactions, including the synthesis and breakdown of small and complex molecules, many of which are necessary for normal vital functions. One of ordinary skill in the cell biological art can polymerize polymeric precursors such as polyacrylamide precursor to cause them to harden and form a polymeric device.

"Microtissues" are cells living in 3D cell cultures cell-cell and cell-matrix interactions and complex transport dynamics for nutrients and cells.

"Polymerize" has the plain meaning of combining or causing to combine to form a polymer. In polymer chemistry, polymerization is reacting monomer molecules together in a chemical reaction to form polymer chains or three-dimensional networks. There are many forms of polymerization, and different systems exist to categorize them.

"Progenitor cells" have the cell biological art-recognized definition of biological cells that have the potential to differentiate into specific types of cells, but which can only divide for a limited number of times. "Bi-potent progenitor cells," e.g., bipotent hepatic progenitor cells found in an adult liver, are progenitor cells that can differentiate into two specific types of cells.

"Selected target cell population" is a set of "target" human 3D microtissue cells that, when a diffusion-driven exchange of metabolites occurs from the metabolizing and hormone-producing cells to the selected target cell population, the function of the selected target cell population may be changed from the natural function to an altered function.

"Standard 96-well tray" microplate is a flat plate with multiple "wells" used as small test tubes. A microplate is a standard tool in analytical research and clinical diagnostic testing laboratories. Robots have been developed specifically to handle microplates for high-throughput assays. Ultra-low attachment (ULA) plates that support 3D cell culture are commercially available, e.g., from Thermo Fisher Scientific, Waltham, MA, USA.

"Standard 384-well tray" microplate is a flat plate with multiple "wells" used as small test tubes. A microplate is a standard tool in analytical research and clinical diagnostic testing laboratories. Robots have been explicitly developed to handle microplates for high-throughput assays. Ultra-low attachment (ULA) plates that support 3D cell culture are commercially available, e.g., from Thermo Fisher Scientific, Waltham, MA, USA.

"Spheroid" microtissues in three-dimensional cell culture have the cell biological art-recognized definition of a type of three-dimensional cell modeling that better simulates a live cell's environmental conditions compared to a two-dimensional cell model, specifically with the reactions between cells and the reactions between cells and the matrix. Fennema et al. (2013) Trends Biotechnol., 31(2), 2. Due to energy and surface area:volume minimization, the sphere shape is generally the terminal structure of cellular self-assembly. Dean et al. (2007) FASEB J., 21 (14), 4005-12.

"Toroid" microtissues in three-dimensional cell culture has the cell biological art-recognized definition of a type of three-dimensional cell modeling alternative in shape to spheroid, being formed in the shape of a torus/ring shape. See, Masuda et al. (2011) "Toroidal Cellular Aggregate for Directed Assembly of Multicellular Structure" and Dean et al. (2008) FASEB J., 21, 4005-12, which describes the directed self-assembly of microtissues with prescribed microscale geometries, such rods, tori, and honeycombs. Dean et al. (2007) FASEB J., 21(14): 4005-12, using micro-molded, nonadhesive agarose hydrogels seeded with rat hepatoma (H35s), human fibroblasts (NHFs), or their mix (1:1), showed that cells could self-assemble rods, tori, and honeycombs. H35s cells formed intact tori and fully intact honeycombs structures with lumens even when released from the mold.

Preferred Embodiments

Method of making micro-molded devices. One having ordinary skill in the cell biological art can fabricate hydrogel devices of the invention utilizing micro-molded nonadhesive hydrogels, as described by Napolitano et al. (2007) Biotechniques 43(4):494, 496-500. In brief, one can use computer-assisted design (e.g., Solid Works, Concord, MA) to create a template of the desired gel features (e.g., a cell seeding chamber, 822 recesses with hemispherical bottoms (800 µm deep×400 µm wide), and media exchange ports). Then, one can generate a wax mold with a prototyping machine (e.g., a ThermoJet rapid prototyping machine), to then generate a negative replicate (e.g., composed of Reprorubber, a fast-curing polydimethysiloxane (PDMS) elastomer (Flexbar, Islandia, NY)). Next, one can fill the negatives (e.g., with Sylgard 184 PDMS (Dow Corning, Midland, MI, USA)) to produce positive replicates. The positive replicates are washed (e.g., with 70% ethanol, then rinsed with distilled water) and autoclaved before use.

One having ordinary skill in the cell biological art can then cast agarose gel bioreactors directly from wax molds, e.g., according to the methods of Napolitano et al. (2007) Biotechniques 43(4):494, 496-500. Aliquots of two g Ultra-Pure Agarose (American Bioanalytical, Natick, MA, USA) are autoclaved as a powder, then 200 mL of sterile $dH_2O$ are added and the agarose dissolved by heating and mixing on a hot plate. The solution is then cooled and approximately 2.75 mL pipetted into each wax mold in a sterile dish.

Alternatively, according to the methods of Napolitano et al. (2007) Biotechniques 43(4):494; 496-500, sterilized 2% agarose solution is pipetted into PDMS molds, and the gel-containing mold placed in a −20° C. freezer for five minutes to harden (but not freeze) the hydrogel. After setting, one can separate hardened agarose bioreactors from the mold using a spatula, transferred to a 6-well plate, and equilibrated overnight with three mL of RPMI 1640 media containing 10% FBS, two mmol/L/mL of I-glutamine, and 100 U/mL of penicillin/streptomycin, at 37° C. in a humidified incubator with a 5% $CO_2$-95% air atmosphere.

One having ordinary skill in the cell biological art can also fabricate agarose hydrogels using the method of Robins et al. (2011) Reproductive Sciences (Thousand Oaks, Calif.) 18(2): 128-35, described a three-dimensional (3D) trophoblast bioreactor to study cellular interactions. Ordinarily, trophoblast cells in vivo form a three-dimensional structure that promotes complex cell-to-cell interactions, which could not be studied with traditional monolayer culture. Robins et al, cast nonadhesive agarose hydrogels from molds using computer-assisted prototyping. In these agarose hydrogels, trophoblast cells formed uniform spheroids consistent with natural trophoblast cell morphology, motility, and vesicle behavior.

Figure 1:
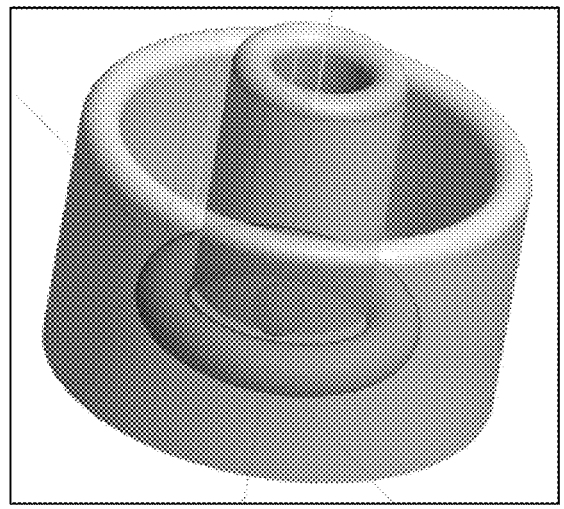
FIG. 1 shows one well of a 96-well plate. The center well was loaded separately from the outer cell. The center well contains the target microtissue (a small central ball) surrounded by the HepaRG cells (toroid) loaded in the outer well. Metabolites can diffuse between these adjacent agarose compartments.

Alternatively, one having ordinary skill in the cell biological art can fabricate a stainless-steel mold, then use the mold to form two compartments from molten agarose (2%) pipetted into a 96-well plate (See, FIG. 1). One can use computer-aided design (CAD) to fabricate the stainless-steel mold.

These two-compartment micro-molds enable the formation of two distinct microtissues: a larger HepaRG toroidal microtissue surrounding a spheroid of the selected target tissue cells. The agarose hydrogel facilitates the diffusion-driven sharing of media and metabolites between the two microtissues. The differences in sizes/cell number of the two microtissues should enable one having ordinary skill in the cell biological art to approximate allometric scaling concerning the liver, the media volume, and the target tissue. One can adjust the number of HepaRG cells seeded. One can adjust the mold to increase or decrease the diameter and, therefore, the size/cell number of the HepaRG toroidal microtissue.

The first compartment is adapted for containing 3D microtissues (spheroid or toroid) of a metabolizing and hormone-producing cell population. In another embodiment, one having ordinary in the cell biological art can seed the first compartment with metabolizing and hormone-producing cells according the methods of Ramaiahgari et al. (2017) Toxicol Sci. 159: 124-136, who described the development of 96- and 384-well 3D spheroid cultures of HepaRG cells in ultra-low attachment plates which support spheroidal differentiation. Ramaiahgari et al. (2017) grew HepaRG cells to form spheroids in 96-well and 384-well ULA plates. The geometry (semi-spherical bottom shape) and low-binding features allowed cells to remain suspended, which facilitated cell-cell adhesions and interactions overtime, resulting in highly differentiated spheroids.

In another embodiment, the liver microtissue in the first compartment is a 3D HepaRG human hepatocyte microtissue toroid, which exhibits stable hallmarks of hepatocyte functionality, including (1) physiologically relevant drug-metabolizing activities, (2) liver enzyme induction, and (3) evidence of biliary excretion functionality.

Ramaiahgari et al. (2017) found that when seeded at a density of 1000 cells per well in a one-step addition (i.e., with no gels, polymers, or spinning), HepaRG cells self-aggregate to form spheroid-like structures without adding exogenous extracellular matrix (ECM) components. From days 1-3, the individual cells HepaRG aggregate, reaching compact spherical units by about day 7 in culture. The diameter of spheroids across a 384-well plate area ~200 µm. In Ramaiaghari's hands, initial cell seeding densities of 1000 cells/well were best for generating an organized spherical structure with higher levels of drug metabolism enzyme activities. Ramaiaghari et al. found that cell numbers greater than 2000 cells/well-formed aggregates but displayed suboptimal structures. Ramaiaghari et al. (2017) optimized cell culture conditions to produce uniform spheroid-like structures and maintain a stable spheroid phenotype with high levels of liver cell morphology-indicative CYP450 enzyme activity.

For optimal cell seeding, one can remove air bubbles that form in the recesses of the hydrogel during equilibration using a vacuum chamber (Lindberg/Blue M, Thermo Scientific, Waltham, MA, USA) before cell seeding. One then aspirates the medium. The desired cells in suspension ($1 \times 10^6$ cells in 200 µl) are then added dropwise to the center of the seeding chamber. Cells settle into the individual recesses for 30-45 min, after which one adds three ml serum medium to each well.

The inventors performed HepaRG spheroid assessments. HepaRG spheroids cultured for 21 days were stained with nuclei dye Hoechst 33342 (ThermoFisher, Waltham, MA, USA) suitable for live-cell imaging assays. The inventors prepared ten ng/ml of Hoechst 33342 in cell culture medium and added this to the spheroids. After a 15-minute incubation, the inventors imaged the spheroids for nuclei and cellular morphology by phase-contrast imaging, taking 20 Z-sections of each spheroid using a high content imager, ImageXpress Micro (Molecular Devices, Sunnyvale, CA, USA). A "maximum intensity projection image" of the spheroid was generated from 20 Z-sections imaged in the nuclei channel from 384-well plates. This "maximum intensity projection image" was analyzed with multi-wavelength cell scoring settings on Metaxpress image analysis software (Molecular Devices, Sunnyvale, CA, USA).

In another embodiment, the first compartment is a larger circular trough (4 mm diameter), in which metabolizing and hormone-producing cells form a toroidal microtissue with $\sim 2 \times 10^5$ cells surrounding the target microtissue. See, Dean et al. (2007) FASEB J., 21(14), 4005-12.

Cryo-preserved human liver HepaRG cells can be seeded into the toroidal liver chamber of the two-compartment well. A range of seeding densities ($2-3 \times 10^5$ cells/well in 200 uL media), and timings of media changes (every 12, 24, or 36 hours post-cell-seeding) can be tested to maximize viability and differentiation. Assessments include (1) RT-PCR for genes involved in xenobiotic metabolism (Phase I and II), hepatic transport (uptake and efflux), and glucose and lipid metabolism, (2) evaluation of glycogen storage (periodic acid Schiffs stain), and (3) immunohistochemical staining for the cholangiocyte marker cytokeratin 19 (CK19), xenobiotic-metabolizing enzyme presence (CYP3A4), and polarization of bile canaliculi (MRP2). Hepatic function can be further determined, for example (a) Phase I metabolism can be evaluated by LC-MS/MS for rate of metabolite formation by CYP1A2 (phenaceting→acetaminophen), CYP2B6 (bupropion→1-hydroxybupropion), and CYP3A4 (midazolam→1-hydroxymidazolam); (b) cytotoxicity can be evaluated with cyclophosphamide with cell viability determined by toroid tissue volume and LIVE/DEAD staining; (c) Phase II processes of glucuronidation, sulfonation, and glutathione conjugation can be evaluated by LC-MS/MS detection of secondary metabolites of phenacetin, bilirubin, and 4-methylumbelliferone; (d) xenobiotic activation of receptor signaling pathways can be evaluated using activators and sentinel gene targets (pregnane X receptor [PXR], rifampicin, CYP3A4; constitutive androstane receptor [CAR], phenobarbital, CYP2B6; aryl-hydrocarbon receptor [AhR]), omeprazole, CYP1A2) [the half-maximal effective concentration ($EC_{50}$) for each activator can be calculated and compared with literature values]. Hepatobiliary transport can be evaluated by incubating HepaRG toroids with 5-chloromethylfluorescein diacetate (CM FDA), a precursor converted into fluorescent glutathione-methylfluorescein, which is excreted into bile canaliculi via MRP2, with and without the MRP2 inhibitor MK571, followed by nuclear counterstaining (Hoechst 33358) and confocal imaging.

In one embodiment, the second compartment can be adapted for containing 3D microtissues of a selected target cell population. One having ordinary skill in the cell biological art can use a 96-well 3D PetriDish® of micromolded agarose, with each well having two compartments that can be separately and sequentially seeded with different cell types. A second compartment is for containing the "target" human 3D microtissue. In another embodiment, the second compartment, located in the center of the plate, is a round micro-well in which the target cells form a single spheroid of 200-2000 cells, depending on the target tissue.

In another embodiment, the target human 3D microtissues are neural microtissues. One having ordinary skill in the cell biological art can make human 3D neural microtissues using either the methods of Birenboim et al. (2013 Mar. 30) J. Neurosci. Methods, 214(1):9-14; the methods of Dingle et al. (2015) Tissue engineering. Part C, Methods, 21(12) 1274-83; or another method known in the cell biological art.

In another embodiment, the target human 3D microtissues are cardiac microtissues. One having ordinary skill in the cell biological art can make human 3D cardiac microtissues using the methods of Desroches et al. (2012) Am. J. Physiol., 302(10): H2031-42.

In another embodiment, the target human 3D microtissues are dental pulp-derived cell microtissues. One having ordinary skill in the cell biological art can make human 3D dental pulp-derived microtissues using the methods of Janjić et al. (2017) BMC Oral Health, 17, 1-87.

Other human 3D microtissues are disclosed in EXAMPLE 2 below.

Curran et al. (2015) TECHNOLOGY, 3(1), 54-63, describes methods and materials to measure the uptake of materials by a 3D spheroid system to evaluate inhibitors of the ABCG2 transporter in drug uptake and penetration. The methods of Curran et al. (2015) can be used to assess the uptake of metabolites by the selected target cell population in the device of the invention.

In one embodiment, the second compartment can also be adapted for containing cells of a selected target cell population in a two-dimensional (2D) form. 2D cell cultures have been used in the cell biological art for many years. 2D cell culture systems grow cells on flat dishes, typically made of plastic. The cells are put onto coated surfaces where they adhere and spread. Despite some advantages of 3D cell culture, 2D cell cultures are still used for the majority of cell cultures because it is comparatively inexpensive, well-established, and well-understood by one of skill in the cell culture art, with a good amount of comparative literature on which one can rely and with easier cell observation and measurement.

Metabolites and hormones from the 3D microtissues in the first compartment can passively diffuse through the permeable wall to the second compartment and from the second compartment to the first compartment. The device can have walls between the first compartment and the second compartment that comprise of a non-adhesive hydrogel having sufficient porosity to permit metabolites and hormones from the 3D microtissues to diffuse from the first compartment to the second compartment and from the second compartment to the first compartment.

The agarose hydrogel allows for diffusion between the first compartment and second compartment, so metabolites produced by the liver microtissue can diffuse to and affect the target microtissue so high-throughput confocal analysis can assess the target cell function.

The agarose walls separating the compartments are optimally high enough so cells can be pipetted separately into each compartment without spillover. The target microtissue is located at a z position that can be readily imaged, for example, using the 20× water objective of the Opera Phenix high throughput confocal microscope.

Allometric scaling. The device format of the invention ensures approximate allometric scaling of the liver microtissue to the volume of media and the target tissue. Hence, metabolites produced by the liver microtissue are of sufficient concentration to mediate an effect on the target tissue. Based on prior studies by Ramaiahgari et al., Toxicol Sci. 2017; 159: 124-136, the allometric scaling can be $\sim 2\times10^5$ HepaRG cells in 200 µl of media or greater.

Conditions supportive of hepatocyte differentiation, viability, and metabolizing capacity in the 96-well platform format and the HepaRG microtissue system. Using the target microtissue media for the co-culture conveniently ensures target microtissue functions most efficiently for these early-stage studies. Still, one having ordinary skill in the cell biological art can use alternative media for each co-culture system, which may be more optimal for HepaRG function.

In one embodiment, one of skill in the cell biological art can use Williams E medium (ThermoFisher, Waltham, MA, USA) supplemented with induction additive MHPIT (Triangle Research Labs, Durham NC).

In another embodiment, one of skill in the cell biological art can use a maintenance medium comprised of Williams E medium supplemented with 15 mM HEPES (ThermoFisher, Waltham, MA), 1×ITS+(Corning, NY, N.Y.), 1× Glutamax (ThermoFisher, Waltham, MA), 100 nM dexamethasone and 25 U/ml penicillin and 25 µg/ml streptomycin.

Method for measuring the toxicity of a test compound. The toxicity of a test compound can be assayed by (a) obtaining the device of the invention; (b) adding the test compound to the first compartment, under conditions so the first compartment contains 3D microtissues in a culture medium; (c) permitting the metabolites from the 3D microtissues in the first compartment to diffuse to the second compartment, under conditions so the second compartment contains 3D microtissues of the selected target cell population in a culture medium; and (d) measuring the effect of the metabolites from the 3D microtissues in the first compartment on the 3D microtissues of the selected target cell population, using an assay that measures a morphological, molecular or functional endpoint, wherein the endpoint provides a safety assessment of the test compound.

The inventors validated the method of the invention, as shown in EXAMPLE 2 below.

The 3D microtissue models can also be tested for their response to other model test compounds. In another embodiment, the HepaRG toroids are cultured for a while in their differentiating media to establish their metabolizing capability. Target tissue cells are then introduced into the center microwell, and the media changed to that appropriate for the target microtissue cell type. After microtissue formation (~1-2 days), the co-culture system is exposed to the precursor across a range of concentrations, with endpoints assessed after 24 and 48 hours. A concentration-response standard curve for each 3D microtissue endpoint in the presence and absence of HepaRG co-culture for the added precursor and metabolite is then calculated, to determine the extent of activation/inactivation resulting from HepaRG metabolism.

To quantify the appearance of the metabolite in the media, one having ordinary skill in the cell biological art can rely on indirect evidence, where the endpoint changes require HepaRG cells. One having ordinary skill in the cell biological art can define success as 2 of 5 target microtissues demonstrating HepaRG-dependent metabolism for an endpoint response.

To ascertain the extent of precursor metabolism, the endpoint change can be referenced to concentration-response standard curves of the target microtissue exposed to precursor and metabolite absent HepaRG toroid.

High throughput workflow. High-throughput screening (HTS) is a method for scientific experimentation mainly used in drug discovery and relevant to the fields of biology and chemistry. A screening facility typically holds a library of stock plates, whose contents are carefully cataloged. These stock plates themselves are not directly used in experiments. Instead, separate assay plates are created as needed. The assay plate is simply a copy of a stock plate, created by pipetting a little liquid from the wells of a stock plate to the corresponding wells of an empty plate. Typically, an integrated robot system consisting of one or more robots transports assay-microplates from station to station for sample and reagent addition, mixing, incubation, and finally readout or detection. An HIS system can usually prepare, incubate, and analyze many plates simultaneously, further speeding the data-collection process. See, Inglese & Auld (2009) Application of High Throughput Screening (HTS) Techniques: Applications in Chemical Biology in Wiley Encyclopedia of Chemical Biology (Wiley & Sons, Inc., Hoboken, NJ) Vol 2, pp 260-274: Macarron et al. (2011) Nat. Rev. Drug Discov. 10(3): 188-195; Michael et al. (2008) ASSAY and Drug Development Technologies 6(5): 637-657.

Other useful techniques known to one having ordinary skill in the cell biological art include confocal microscopy, histological analysis, immunostaining, and liquid chromatography/mass spectroscopy (LC-MS).

Microscopy, image, and data analysis. For horizontal-view microscopy, one can harvest spheroids according to the methods of Ramaiahgari et al. (2017) Toxicol. Sci. 159: 124-136, by inverting the gels in 6-well plates and centrifuging at 800 rpm for 6 min. The spheroids are then resuspended in medium and 30 µl added to each viewing gel. Using a Mitutoyo FS-110 microscope modified to lie horizontally, bright-field images of the front face of the spheroids can be taken.

Ramaiahgari et al. (2017) measured morphological changes with ImageJ software (Rasband, ImageJ, U.S. National Institutes of Health, Bethesda, MD, USA, http://rsb.info.nih.gov/ij/, 1997-2006). Ramaiahgari et al. (2017)

used the obtained horizontal-view images to compute spheroid aspect ratios from spheroid height and width. The length of a rod was the length of a line drawn from end to end of the structure (long axis length). The core circumference of a toroid can be measured as a continuous circumferential line located at the estimated midpoint of the perpendicular width of the toroid.

Cell viability assessments and microtissue viability assessments can be performed using the Live/Dead Viability/Cytotoxicity kit (Invitrogen, Carlsbad, CA, USA). Cells were rinsed with PBS and stained with two μM calcein-AM and four μM ethidium homodimer-1 (in 300 μl PBS) at 37° C. for 30 min, followed by image acquisition.

The following Examples are provided to illustrate the invention and should not be considered to limit its scope.

EXAMPLES

Example 1

HepaRG Cells Successfully Formed 3D Microtissues in the Device of the Invention.

Figure 2A:
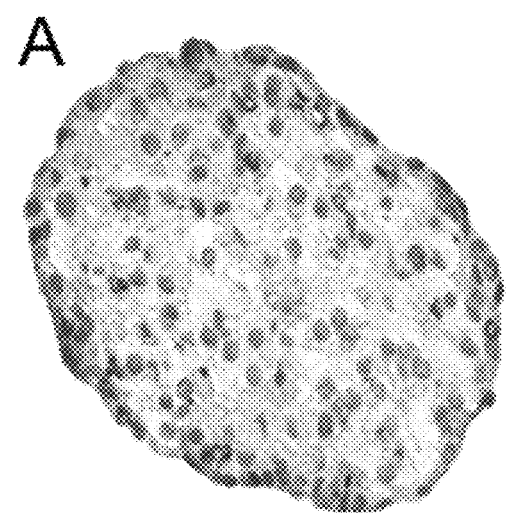
FIG. 2A is a picture of HepaRG spheroids, stained positive by immunohistochemistry for multidrug resistance protein 2.

In the agarose micro-mold device of the invention, HepaRG cells successfully formed 3D microtissues consisting of cells with abundant cytoplasm that expressed the multidrug resistance protein 2 (MRP2). See, FIG. 2A.

Figure 2B:
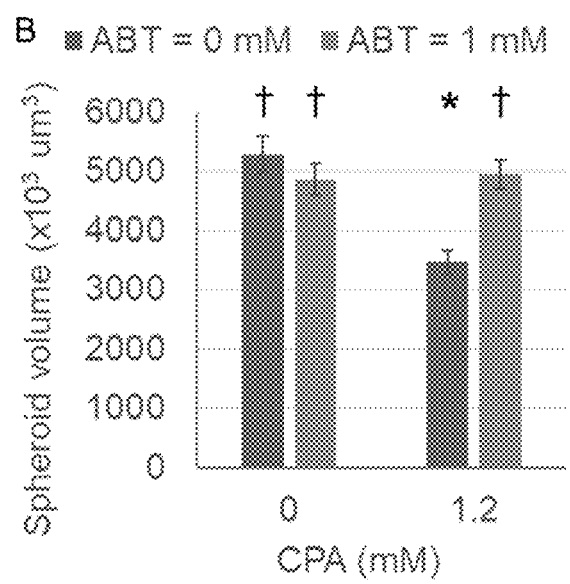
FIG. 2B is a chart showing the change in HepaRG spheroid volume as an indicator of cytotoxicity induced by cyclophosphamide (CPA) with or without 1-aminobenzotriazol (ABT). The inventors analyzed the data with two-way ANOVA with Tukey's LSD means. P=0.05. Bars with different symbols are statistically significantly different. Adding ABT inhibits the metabolism of the CPA parent compound to its toxic metabolite, thus preserving the viability of the HepaRG cells and maintaining the volume.

The HepaRG 3D microtissues exhibit xenobiotic metabolism, as shown by exposure to cyclophosphamide (CPA), a prodrug that requires bioactivation by cytochrome P450 enzymes (CYPs) to form cytotoxic metabolites. Exposure of 10-day old HepaRG 3D microtissues to 1.2 mM CPA caused cell death and a significant reduction in spheroid volume (compare blue bars, FIG. 2B). Co-exposure of CPA with the broad-spectrum CYP inhibitor 1-aminobenzotriazol (ABT; one mM) abolished the cytotoxic effects of CPA on HepaRG 3D microtissues by inhibiting the metabolism of CPA to its toxic metabolites (compare green bars, FIG. 2B). Similar results were seen with 21-day old HepaRG 3D microtissues. Thus, the inventive system maintains xenobiotic-metabolizing activity over multiple weeks allowing us to assess the cumulative effects of repeated doses more reflective of human exposures.

Figure 2C:
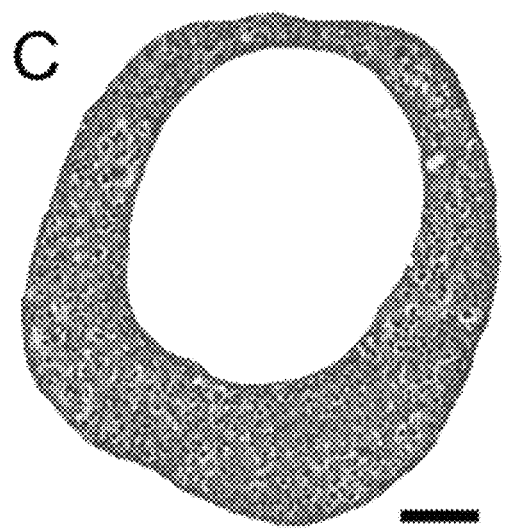
FIG. 2C is a picture showing hematoxylin and eosin (H&E) stained toroid-shaped HepaRG microtissues. Scale bars=100 µm.

Finally, the inventors successfully made stable toroidal HepaRG microtissues (FIG. 2C), a shape allowing maximal cell seeding to optimize the allometric scaling of co-culture systems.

Example 2

Validating the Utility of the Integrated Liver—3D Microtissue Platform

Using the integrated liver-3D microtissue platform, one having ordinary skill in the cell biological art can expose the 3D microtissues to model test compounds whose toxicity is altered by hepatic metabolism. See, e.g., TABLE 1. The model test compounds (toxicants) were chosen for their known targeting of the 3D microtissue cell type, and the requirement that the liver metabolize an innocuous precursor to a toxic/biologically active metabolite (prostate, lung, brain), or that a toxic precursor be inactivated by liver metabolism (ovary, heart).

TABLE 1

Model test toxicants tested in the integrated HepaRG-3D microtissue system

| Microtissue | Precursor | Metabolites | Endpoint |
| --- | --- | --- | --- |
| Prostate | dehydroepiandrosterone | 4-androstenedione-17β-testosterone | androgen-dependent proliferation by spheroid volume and nuclear counts |
| Ovary | α-naphthoflavone (ANS) | oxide & hydroxy metabolites | reversal of ANS inhibition of proliferation via the AhR pathway; spheroid volume & BrdU |
| Lung | Naphthalene | naphthalene epoxide | epithelial cell cytotoxicity by histopathology, spheroid volume, & propidium iodide |
| Brain | Parathion | paraoxon | acetylcholinesterase activity, LDH in media, propidium iodide, βiii-tubulin & GFAP IHC |
| Heart | terfenadine (cardiotoxic) | fexofenadine (non-cardiotoxic) | action potential prolongation, pro-arrhythmic after-depolarizations |

OTHER EMBODIMENTS

Specific compositions and methods of the collagen microfiber scaffolds have been described. The detailed description in this specification is illustrative and not restrictive or exhaustive. The detailed description should not limit the disclosure to the precise form disclosed. Other equivalents and modifications besides those already described are possible without departing from the inventive concepts described in this specification, as persons skilled in the cell biological art will recognize. When the specification or claims recite method steps or functions in order, alternative embodiments may perform the functions in a different order or substantially concurrently. The inventive subject matter should not be restricted except in the spirit of the disclosure.

When interpreting the disclosure, all terms should be interpreted in the broadest possible manner consistent with the context. Unless otherwise defined, all technical and scientific terms used in this specification have the same meaning as commonly understood by one having ordinary skill in the cell biological art. This invention is not limited to the particular methodology, protocols, reagents, and the like described in this specification and can vary in practice. The terminology used in this specification should not limit the scope of the invention, which is defined solely by the claims.

All patents and publications cited throughout this specification are expressly incorporated by reference to disclose and describe the materials and methods that might be used with the technologies described in this specification. The publications discussed are provided solely for their disclosure before the filing date. They should not be construed as an admission that the inventors may not antedate such disclosure under prior invention or for any other reason. If there is an apparent discrepancy between a previous patent or publication and the description provided in this specification, the specification (including any definitions) and claims shall control. All statements as to the date or representation as to the contents of these documents are based on the information available to the applicants and constitute no admission as to the correctness of the dates or contents of these documents. The dates of publication provided in this specification may differ from the actual publication dates. If there is an apparent discrepancy between a publication date provided in this specification and the actual publication date supplied by the publisher, the actual publication date shall control.

The terms "comprises" and "comprising" should be interpreted as referring to elements, components, or steps in a non-exclusive manner, indicating that the referenced elements, components, or steps may be present, used, or combined with other elements, components, or steps. The singular terms "a," "an," and "the" include plural referents unless context indicates otherwise. Similarly, the word "or" should cover "and" unless the context indicates otherwise. The abbreviation "e.g." is used to indicate a non-limiting example and is synonymous with the term "for example."

When a range of values is provided, each intervening value, to the tenth of the unit of the lower limit, unless the context dictates otherwise, between the upper and lower limit of that range and any other stated or intervening value in that range of values.

Some embodiments of the technology described can be defined according to the following numbered paragraphs:

A device comprising at least a first compartment and a second compartment, with a permeable wall between the first compartment and the second compartment; (a) wherein the first compartment is adapted for containing three-dimensional (3D) metabolizing and hormone-producing microtissues, and wherein the first compartment can be seeded with cells from a cell population; (b) wherein the second compartment is adapted for containing three-dimensional (3D) microtissues of a selected target cell population, and wherein the second compartment can be seeded with cells from a selected target cell population, and (c) wherein metabolites and hormones from the 3D microtissues in the first compartment can passively diffuse through the permeable wall to the second compartment and from the second compartment into the first compartment.

The device described above, wherein the 3D microtissue in the first component is allometrically scaled to deliver metabolites and to the cells in the second compartment.

The device described above, wherein the 3D microtissue in the first component comprises at least 200,000 hepatocytes in the compartment.

The device described above, wherein the walls between the first compartment and the second compartment comprise a non-adhesive hydrogel having sufficient porosity to permit metabolites and hormones from the 3D microtissues to diffuse from the first compartment to the second compartment and from the second compartment to the first compartment.

The device described above, wherein (a) the first compartment contains 3D microtissues in a culture medium; and (b) the second compartment contains 3D microtissues of the selected target cell population in a culture medium.

The device described above, wherein the device fits in a standard multi-well plate.

A method of making a device having at least a first compartment adapted for containing three-dimensional (3D) microtissues and a second compartment adapted for containing three-dimensional (3D) microtissues of a selected target cell population, wherein metabolites and hormones from the 3D liver microtissues can passively diffuse from the first to the second compartment and from the second compartment to the first compartment, comprising the steps of (a) placing a mold that forms two compartments into a standard multi-well plate; (b) adding a liquid non-adhesive hydrogel to the mold in the well, and (c) allowing the non-adhesive hydrogel to harden, so the non-adhesive hydrogel has sufficient porosity to permit metabolites and hormones from the 3D microtissues to diffuse from the first compartment to the second compartment and from the second compartment to the first compartment.

A method for measuring the toxicity of a test compound, comprising the steps of (a) obtaining the device of claim 1; (b) adding the test compound to the first compartment, under conditions so the first compartment contains 3D microtissues in a culture medium; (c) permitting the metabolites from the 3D microtissues in the first compartment to diffuse to the second compartment, under conditions so the second compartment contains 3D microtissues of the selected target cell population in a culture medium; (d) measuring the effect of the metabolites from the 3D microtissues in the first compartment on the 3D microtissues of the selected target cell population, using an assay that measures a morphological, molecular or functional endpoint, wherein the endpoint provides a safety assessment of the test compound.

The method of toxicity measurement described above, wherein the assay is amenable to a high throughput workflow.

The method of toxicity measurement described above, wherein the assay is selected from the group consisting of confocal microscopy, histological analysis, immunostaining, and liquid chromatography/mass spectroscopy (LC-MS).

A metal master mold capable of forming an agarose device in a 96-well plate or a 384-well plate. The metal master mold is useful for forming a two-compartment device in any well of a 96-well plate or a 384-well plate.

The metal master mold described above, further comprising the two-compartment device.

A two-compartment agarose device in a well of the 96-well plate or the 384-well plate.

A molded agarose gel, comprising a first compartment containing a three-dimensional (3D) ring of tissue and a second compartment capable of containing target cells.

The molded agarose gel described above, where the three-dimensional (3D) ring of tissue is a ring of liver tissue.

The molded agarose gel described above, where the target cells attach to the bottom of a 96-well plate or a 384-well plate.

The molded agarose gel described above, where the target cells comprise a three-dimensional (3D) spheroid of cells.

The invention claimed is:

1. A device comprising at least a first compartment and a second compartment, with a central permeable wall between the first compartment and the second compartment; the permeable wall being a cell barrier that is impermeable to cells but permeable to small molecules, biomolecules, and proteins including hormones, without requiring a use of an impermeable wall with one or more capillary openings;
    (a) wherein the first compartment is in an opening in a shape of a toroid, surrounding the central permeable wall acting as a molecule-permeable barrier, with a first floor and an outer wall adapted for containing three-dimensional (3D) metabolizing and hormone-producing microtissues, and wherein the first compartment can be seeded with cells from a cell population and the seeded cells will grow into one or more 3D microtissues surrounding the central cell barrier or permeable wall; the first compartment operative to accept a test compound, and the one or more 3D microtissues being capable of metabolizing the test compound;
    (b) wherein the central permeable wall includes a hollow center with a second floor forming the second compartment surrounded by the central permeable wall;
    (c) wherein the second compartment is adapted for containing cells of a selected target cell population that do not cross over to the first compartment, and wherein the second compartment can be seeded with cells, cells in a gel, or cells in a liquid from a selected target cell population and said cells are operative to grow into one or more target cells in a form of one or more microtissues, a two-dimensional (2D) attached monolayer of cells, and/or into a 3D spheroid; and
    (d) whereupon if the 3D microtissue(s) metabolizes the test compound, metabolites and hormones resulting from one or more effects of the test compound on the 3D microtissues in the first compartment can passively diffuse through the central permeable wall to the one or more target cells in the second compartment and from the second compartment into the first compartment.

2. The device of claim 1, wherein the 3D microtissue in the first compartment is allometrically scaled to deliver metabolites and to the microtissue in the second compartment.

3. The device of claim 1, wherein the wall between the first compartment and the second compartment comprise a non-adhesive hydrogel having sufficient porosity to permit metabolites and hormones from the 3D microtissues to diffuse from the first compartment to the second compartment and from the second compartment to the first compartment.

4. The device of claim 1, wherein
    (a) the first compartment contains 3D microtissues in a culture medium; and
    (b) the second compartment contains the selected target cell population in a culture medium.

5. The device of claim 1, wherein the device fits in one well of a standard multi-well plate.

6. A method for measuring the toxicity of a test compound, comprising the steps of
    (a) obtaining the device of claim 1;
    (b) adding the test compound to the first compartment, under conditions so the first compartment contains 3D microtissues in a culture medium;
    (c) permitting the metabolites from the 3D microtissues in the first compartment to diffuse to the second compartment, under conditions, so the second compartment contains microtissues of the selected target cell population in a culture medium;
    (d) measuring the effect of the metabolites from the 3D microtissues in the first compartment on the microtissues of the selected target cell population, using an assay that measures a morphological, molecular, or functional endpoint, wherein the endpoint provides a safety assessment of the test compound.

7. The method of claim 6, wherein the assay is amenable to a high throughput workflow.

* * * * *